(12) United States Patent
Li et al.

(10) Patent No.: US 9,057,709 B2
(45) Date of Patent: Jun. 16, 2015

(54) AIRFLOW-ORGANIZATION TESTING METHOD FOR A CLEAN ROOM AND SYSTEM USING THE SAME METHOD

(71) Applicant: BEIJING BOE OPTOELECTRONICS TECHNOLOGY CO., LTD., Beijing (CN)

(72) Inventors: Li Li, Beijing (CN); Wanshi Jin, Beijing (CN)

(73) Assignee: Beijing BOE Optoelectronics Technology Group Co., Ltd., Beijing (CN)

( * ) Notice: Subject to any disclaimer, the term of this patent is extended or adjusted under 35 U.S.C. 154(b) by 94 days.

(21) Appl. No.: 13/704,363

(22) PCT Filed: Sep. 21, 2012

(86) PCT No.: PCT/CN2012/081773
§ 371 (c)(1),
(2) Date: Dec. 14, 2012

(87) PCT Pub. No.: WO2013/044761
PCT Pub. Date: Apr. 4, 2013

(65) Prior Publication Data
US 2014/0061471 A1 Mar. 6, 2014

(30) Foreign Application Priority Data
Sep. 26, 2011 (CN) .......................... 2011 1 0289975

(51) Int. Cl.
*G01N 21/00* (2006.01)
(Continued)

(52) U.S. Cl.
CPC *G01N 21/94* (2013.01); *G01P 5/10* (2013.01); *G01P 5/001* (2013.01); *G01J 5/0014* (2013.01); *G01J 2005/0085* (2013.01); *G01J 2005/0077* (2013.01)

(58) Field of Classification Search
CPC ...................................................... G01J 5/0014
USPC .................................... 250/338.1–338.5, 340
See application file for complete search history.

(56) References Cited

U.S. PATENT DOCUMENTS 4,067,771 A    1/1978 Rubin
(Continued)

FOREIGN PATENT DOCUMENTS

CN           88101631         11/1988
(Continued)

OTHER PUBLICATIONS

International Search Report and Written Opinion (with English translation) for International (PCT) Patent Application No. PCT/CN2012/081773 mailed Jan. 10, 2013, 29 pages.
(Continued)

*Primary Examiner* — Kiho Kim
(74) *Attorney, Agent, or Firm* — Sheridan Ross P.C.

(57) ABSTRACT

An airflow-organization testing method for a clean room and a system using the same method are disclosed. The airflow-organization testing method for a clean room uses a thermal imaging device to detect a sample gas-flow formed by a sample gas in the clean room, and the sample gas has a temperature difference from ambient air. The airflow-organization testing system for a clean room includes a sample gas supplier and a thermal imaging device, and the thermal imaging device can continuously detect a spatial position of the sample gas and display it on a display, thereby improving detection precision and expanding detection range.

13 Claims, 1 Drawing Sheet

(51) Int. Cl.
  G01N 21/94 (2006.01)
  G01P 5/10 (2006.01)
  *G01P 5/00* (2006.01)
  *G01J 5/00* (2006.01)

(56) References Cited

U.S. PATENT DOCUMENTS

| | | | |
|---|---|---|---|
| 4,829,773 A | 5/1989 | Matsumura et al. | |
| 4,896,532 A | 1/1990 | Schmalz | |
| 5,127,264 A | 7/1992 | Schmalz | |
| 5,457,989 A | 10/1995 | Minoshima | |
| 6,607,435 B2 * | 8/2003 | Yokoyama et al. | 454/187 |

FOREIGN PATENT DOCUMENTS

| | | |
|---|---|---|
| CN | 101303364 | 11/2008 |
| CN | 102650604 | 8/2012 |
| JP | H02-031168 | 2/1990 |
| JP | H03-135773 | 6/1991 |
| JP | H06-050274 | 2/1994 |
| JP | H07-225156 | 8/1995 |
| JP | H10-132840 | 5/1998 |
| WO | WO 88/05917 | 8/1988 |

OTHER PUBLICATIONS

International Preliminary Report on Patentability for International (PCT) Patent Application No. PCT/CN2012/081773 mailed Apr. 10, 2014, 12 pages.
Official Action (with English translation) for Chinese Patent Application No. 201110289975.7 dated Jun. 4, 2013, 12 pages.
Official Action (with English translation) for Chinese Patent Application No. 201110289975.7 dated Jan. 13, 2014, 12 pages.
Official Action (with English translation) for Korean Patent Application No. 10-2012-7031147 dated Dec. 23, 2013, 6 pages.
Official Action (with English translation) for Korean Patent Application No. 10-2012-7031147 dated May 27, 2014, 5 pages.
Schmalz "Infrared visualized air turbulence," Proceedings of SPIE, SPIE—International Society for Optical Engineering, US, vol. 1313, Jan. 1, 1990, pp. 278-281.
Decision on Appeal with English Translation for China Patent Application No. 7031147, dated Jan. 21, 2015, 18 pages.
Official Action with English Translation for China Patent Application No. 201110289975.7, dated Dec. 8, 2014, 10 pages.
Extended Search Report for European Patent Application No. 12778032.8, dated Jan. 27, 2015, 7 pages.
Official Action with English Translation for China Patent Application No. 201110289975.7, dated Apr. 13, 2015, 13 pages.

* cited by examiner

AIRFLOW-ORGANIZATION TESTING METHOD FOR A CLEAN ROOM AND SYSTEM USING THE SAME METHOD

CROSS REFERENCE TO RELATED APPLICATIONS

This application is a national stage application under 35 U.S.C. 371 and claims the benefit of PCT Application No. PCT/CN2012/081773 having an international filing date of Sep. 21, 2012, which designated the United States, which PCT application claimed the benefit of Chinese Application No. 201110289975.7 filed Sep. 26, 2011, the disclosure of both the above-identified applications are incorporated herein by reference.

TECHNICAL FIELD

The present invention relates to an airflow-organization testing method for a clean room and a testing system.

BACKGROUND

In fields such as medical and pharmaceutical industries, and liquid crystal display apparatus or semiconductor device manufacturing industries, harmful bacteria, impurity particles or particulate matters have a significant impact on product quality. Therefore, it becomes very important for the quality of a product whether the cleanliness meets a preset standard. In order to ensure the cleanliness of a clean room, it is particularly important to accurately grasp the airflow distribution characteristics in the clean room. Visual testing of clean airflow is one of the most effective methods for accurately grasping air distribution characteristics of a clean room. As shown in FIG. 1, at present, organic solvent is mainly used within a smoke-and-fog supplier, and also there is a case of using water vapor. Organic solvent can be used to make smoke-generation gas particles smaller and droplets smaller and more uniform, and incur a relatively increased amount of fog-generation and good density uniformity. With the characteristics of an gaseous state of an organic solvent and water vapor showing white or other colors in the air, the movement of the organic solvent gas-flow in the clean room can be observed, and therefore the airflow distribution situation in a clean room can be tested, thereby observing whether there is a phenomenon such as a hazardous vortex or an abnormal circulation, etc.

SUMMARY

The inventors have found that, the aforesaid testing method has the following defects: it faces various degrees of organic solvent contamination; it depends on visual observation of test personnel during a testing process; it is difficult to observe and has poor accuracy; it is difficult to perform a test within a large-area space due to a short smoke-generation distance and a limited amount of visible fog-generation.

The present invention is conceived to overcome at least part of the above-mentioned defects.

According to an embodiment of the present invention, there is provided an airflow-organization testing method for a clean room, and the testing method uses a sample gas with temperature difference from ambient air to form a sample gas-flow in the clean room.

For example, the testing method may comprise the following steps: releasing the sample gas, and the sample gas forming the sample gas-flow along with a clean room airflow; performing an infrared detection on the sample gas-flow and obtaining an infrared radiation energy distribution graph; converting the infrared radiation energy distribution graph into an infrared thermal image; and in accordance with change relationship of space verses time of the infrared thermal image, calculating airflow distribution characteristics in the clean room.

Preferably, the infrared detection is performed continuously.

Preferably, the testing method further comprises displaying the infrared thermal image.

The airflow distribution characteristics, for example, comprise at least one item of wind speed, three-dimensional wind direction and vortex of a tested area.

For example, calculating a wind speed of a tested area comprises: taking a distance by which the detected sample gas moves in a unit of time as the wind speed of the tested area; calculating a three-dimensional wind direction comprises: taking a relative positional change of the detected sample gas with respect to a reference point in a unit of time as the three-dimensional wind direction of the tested area.

According to another embodiment of the present invention, there is provided an airflow-organization testing system for a clean room, and the testing system comprises a sample gas supplier, and the sample gas supplier releases a sample gas with temperature difference from ambient air to form a sample gas-flow in the clean room.

Preferably, the sample gas is liquid nitrogen, dry ice, or water vapor.

The testing system may further comprise: a thermal imaging device, which performs the infrared detection on the sample gas-flow to obtain the infrared radiation energy distribution graph, and converts the infrared radiation energy distribution graph into an infrared thermal image; and an analysis device, which calculates airflow distribution characteristics in the clean room based on the infrared thermal image.

Preferably, the thermal imaging device continuously performs the infrared detection.

Preferably, the thermal imaging device displays the infrared thermal image.

The thermal imaging device may comprise: an infrared detector, which performs the infrared detection on the sample gas-flow, and obtains then infrared radiation energy distribution graph; a photosensitive unit, which scans the infrared radiation energy distribution graph to obtain electrical signals; and a video converter, which converts the obtained electrical signals into the infrared thermal image.

The airflow distribution characteristics, for example, comprise at least one item of wind speed, three-dimensional wind direction and vortex of a tested area.

Preferably, the testing system further comprises a temperature variation correction unit, for compensating the infrared thermal image in accordance with temperature variations of the sample gas.

DETAILED DESCRIPTIONS

Figure 1:
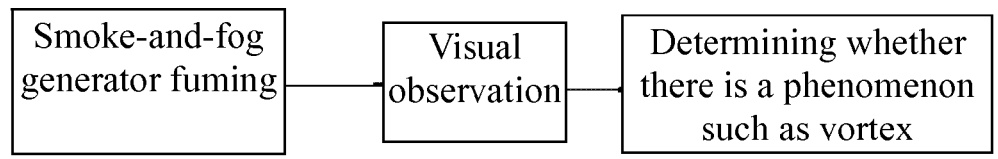
FIG. 1 is a schematic diagram of the principle of an existing detection method.

Below, embodiments of the present invention will be described in detail in connection with the descriptions for the embodiments and the accompanying drawings of the specification.

The airflow-organization testing method for a clean room according to an embodiment of the present invention uses a sample gas-flow formed in the clean room by sample gas, and the sample gas is a kind of gas with temperature difference from ambient air. The sample gas moves along with the ambient airflow and thus forms the sample gas-flow. Due to the existence of the temperature difference, based on thermal imaging, it is possible to quite accurately detect the sample gas-flow, record the direction of the gas-flow, and calculate the velocity of the gas-flow. It is also possible to display the temperature distribution on a display apparatus and visually observe the dynamic conditions of the sample gas-flow, thereby observing the dynamic conditions of the ambient airflow.

The airflow-organization testing method for a clean room according to an embodiment of the present invention comprises the following steps:

releasing sample gas, the sample gas forming a sample gas-flow along with clean room airflow;

performing an infrared detection on the sample gas-flow and obtaining an infrared radiation energy distribution graph;

converting the infrared radiation energy distribution graph into an infrared thermal image; and in accordance with change relationship of space versus time of the infrared thermal image, calculating airflow distribution characteristics in the clean room.

A main requirement to the sample gas is that its density is equivalent to, i.e., equal to or close to, the density of the ambient air, so as to reduce inaccurate measurement caused by gravitational reasons. The sample gas can flow with the ambient air but will float or sink due to the difference in density, and therefore will not give rise to interference to the detection results.

With respect to the feature of existence of a temperature difference between the sample gas and the ambient air, a preferably-used detection method is an infrared detection method, of which the obtained detection result is an infrared radiation energy distribution graph. After the infrared radiation energy distribution graph is scanned into an infrared thermal image, it is possible to perform calculation, and obtain testing results of a wind speed and three-dimensional wind directions in the area to be tested. An method for the calculation is the distance by which the detected sample gas moves in a unit of time equals to the wind speed of the tested area; taking, for example, with the thermal imaging device as a reference point, a relative positional change of the detected sample gas with respect to the reference point in a unit of time is the three-dimensional wind directions in the tested area.

At the same time, researchers can observe whether there is a phenomenon such as vortex or abnormal airflow in the area to be tested according to the infrared thermal image, and then determine whether the vortex measured has an adverse effect on the cleanliness, and whether the abnormal airflow belongs to an unfavorable airflow which flows from a place of low cleanliness to a place of high cleanliness.

At the same time, researchers can accurately measure air exchange times within a unit of volume in the clean room according to the gas velocity of the gas-flow and the directions of the gas-flow, thereby determining the cleanliness level of the clean room.

The airflow-organization testing method for a clean room according to an embodiment of the present invention uses a thermal imaging device to detect flowing conditions of the sample gas, which achieves a dynamic detection, and obtains more accurate test results. The sample gas preferably uses a kind of gas, such as liquid nitrogen, dry ice or water vapor, with temperature difference from ambient air, so as to avoid bringing contamination into the clean room; the detection device preferably uses an infrared detection system, which has mature technology and high test-precision.

The airflow-organization testing system for a clean room according to an embodiment of the present invention comprises a sample gas supplier, and the sample gas supplier releases a sample gas with temperature difference from ambient air to form a sample gas-flow in the clean room.

The sample gas preferably uses a kind of gas, such as liquid nitrogen, dry ice or water vapor, with temperature difference from ambient air.

The testing system may further comprise: a thermal imaging device, which performs an infrared detection on the sample gas-flow to obtain an infrared radiation energy distribution graph, and converts the infrared radiation energy distribution graph into an infrared thermal image; and an analysis device, which, based on the infrared thermal image, calculates airflow distribution characteristics in the clean room.

The thermal imaging device may comprise: an infrared detector, which is used for continuous detection on the specific distribution of the sample gas and the ambient air, and which obtains an infrared radiation energy distribution graph; a photosensitive unit, which scans the infrared radiation energy distribution graph to obtain electrical signals; a video converter, which converts the obtained electrical signals into an infrared thermal image; a display device, which displays the video signals of the obtained infrared thermal image to facilitate researchers in visually observing the airflow conditions, and determining whether there is a phenomenon such as vortex. Some vortexes have an adverse effect on the cleanliness, so that objects such as impurities or particles cannot be carried outside by the airflow to the outside. Some vortexes have little effect on cleanliness, but it is helpful for further research and improvement work to grasp the positions and causes of these vortexes.

Figure 2:
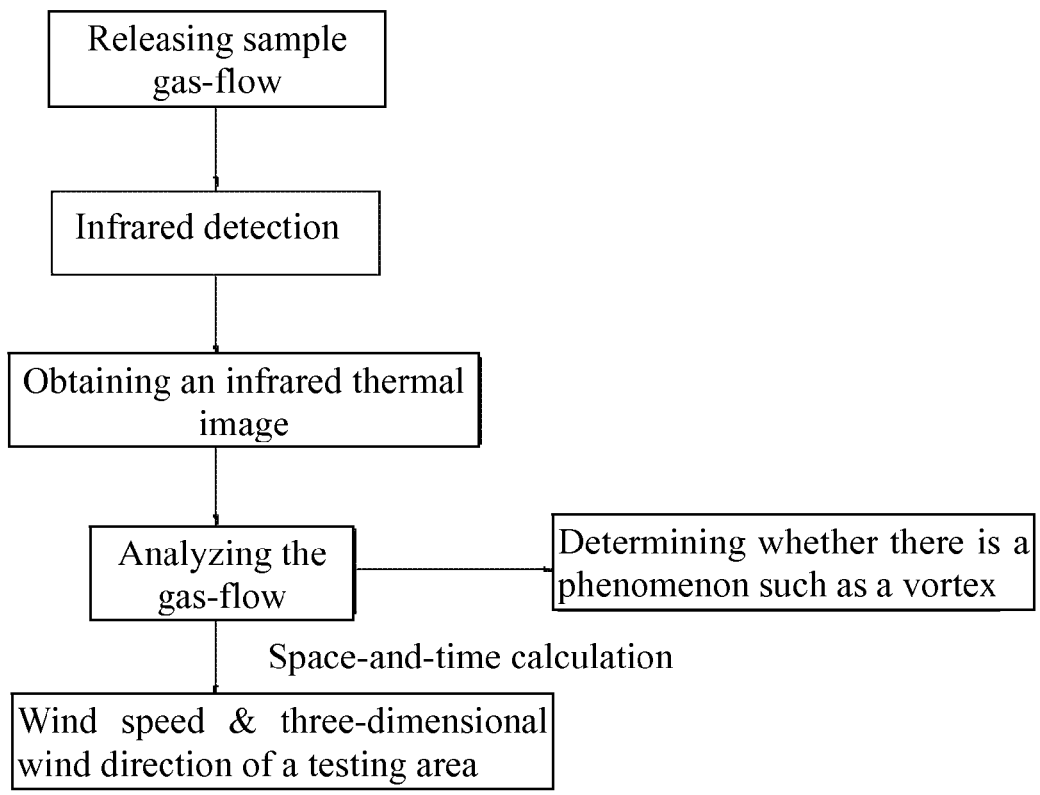
FIG. 2 is a schematic diagram of an example of the airflow-organization testing method according to an embodiment of the present invention.

Below, an example of the testing method according to an embodiment of the present invention will be described with reference to FIG. 2. The testing method comprises the following steps:

releasing low-temperature or high-temperature sample gas, and the sample gas forming a sample gas-flow along with a clean room airflow so that gas temperature difference is formed in a space to be tested;

performing an infrared detection on the sample gas-flow and obtaining an infrared radiation energy distribution graph;

converting the infrared radiation energy distribution graph, and obtaining an infrared thermal image; and based on the infrared thermal image, analyzing the distribution characteristics of the airflow, for example, wind speed, three-dimensional wind direction and/or presence of vortex in the tested area.

The infrared detection method performed to the sample gas-flow is a preferred method, because the infrared detection technologies have become mature and can obtains high-accurate results. Using the infrared detection method to detect the spatial positions that the sample gas reaches, a dynamic data result can be formed by continuous detection.

In this example, the method utilizes an infrared detector and obtains a measured infrared radiation energy distribution graph of a target gas-flow such as liquid nitrogen, dry ice or water vapor. Then, it utilizes a photosensitive element to scan the obtained energy-distribution-graph and converts the infrared radiation energy into electrical signals. Next, the electrical signals are subject to an amplification process and are converted into standard video signals. The video signals are displayed through a TV screen or a monitor as a visible infrared thermal image. Through combination calculation on space-and-time of the changing displacement of the infrared thermal image, results of a wind speed and a three-dimensional wind direction of the tested area are obtained, thereby determining the direction and speed of the gas-flow. At the same time, with continuous analysis of the recorded infrared thermal images, researchers can determine whether there is a phenomenon affecting the cleanliness, such as an adverse vortex or an abnormal airflow, etc., in the clean room to be detected by observing the infrared thermal images.

In addition, it is possible to add a temperature variation correction unit of the sample gas and, by automatically converting the temperature of the tested sample gas and the temperature of the tested space, to obtain a temperature variation of the sample gas. According to the results, the infrared thermal image(s) can be compensated for the displayed colors; and according to the temporal changes of the displacement in space, parameters such as wind speed, wind direction, and amount of gas-flow are accurately calculated and measured, and further the cleanliness of the clean room is accurately evaluated, and so on.

While the above description is merely the preferred embodiments of the present invention, the protection scope of the present invention is not limited thereto. Within the technical scope disclosed by the present invention, modifications or alterations that are easily devised by those skilled who are familiar with the art, should be included within the protection scope of the present invention. Therefore, the protection scope of the present invention should be defined by the scope of the claims.

The invention claimed is:

1. An airflow-organization testing method for a clean room, comprising the steps of:
    releasing a sample gas having a temperature that is different from a temperature of an ambient air in the clean room to form a sample gas-flow in the clean room, wherein a density of the sample gas is equivalent to a density of the ambient air; and
    obtaining an infrared thermal image of the sample gas-flow.

2. The airflow-organization testing method for a clean room according to claim 1, wherein the testing method comprises following steps:
    releasing the sample gas to form the sample gas-flow along with a clean room airflow;
    performing an infrared detection on the sample gas-flow and obtaining an infrared radiation energy distribution graph;
    converting the infrared radiation energy distribution graph into the infrared thermal image; and
    in accordance with change relationship of space versus time of the infrared thermal image, calculating airflow distribution characteristics in the clean room.

3. The airflow-organization testing method for a clean room according to claim 2, wherein the infrared detection is performed continuously.

4. The airflow-organization testing method for a clean room according to claim 2, wherein the testing method further comprises displaying the infrared thermal image.

5. The airflow-organization testing method for a clean room according to claim 2, wherein the airflow distribution characteristics comprises at least one item of wind speed, three-dimensional wind direction and vortex of a tested area.

6. The airflow-organization testing method for a clean room according to claim 5, wherein calculating a wind speed of the tested area comprises: taking a distance by which the detected sample gas moves in a unit of time as the wind speed of the tested area; calculating a three-dimensional wind direction comprises: taking a relative positional change of the detected sample gas with respect to a reference point in a unit of time as the three-dimensional wind direction of the tested area.

7. An airflow-organization testing system for a clean room, wherein the system comprises:
    a sample gas supplier configured to release a sample gas comprising a temperature that is different from a temperature of ambient air to form a sample gas-flow in the clean room;
    a thermal imaging device, which is configured to perform an infrared detection on the sample gas-flow to obtain an infrared radiation energy distribution graph, and convert the infrared radiation energy distribution graph into an infrared thermal image; and
    a temperature variation correction unit, which is configured to compensate the infrared thermal image in accordance with temperature variations of the sample gas.

8. The airflow-organization testing system for a clean room according to claim 7, wherein the sample gas comprises at least one of liquid nitrogen, dry ice, and water vapor.

9. The airflow-organization testing system for a clean room according to claim 7, wherein the testing system further comprises:
    an analysis device, which calculates airflow distribution characteristics in the clean room based on the infrared thermal image.

10. The airflow-organization testing system for a clean room according to claim 9, wherein the thermal imaging device continuously performs the infrared detection.

11. The airflow-organization testing system for a clean room according to claim 9, wherein the thermal imaging device displays the infrared thermal image.

12. The airflow-organization testing system for a clean room according to claim 9, wherein the thermal imaging device comprises:
    an infrared detector, which performs the infrared detection on the sample gas-flow, and obtains the infrared radiation energy distribution graph;
    a photosensitive unit, which scans the infrared radiation energy distribution graph to obtain electrical signals; and
    a video converter, which converts the obtained electrical signals into the infrared thermal image.

13. The airflow-organization testing system for a clean room according to claim 9, wherein the airflow distribution characteristics comprises at least one item of wind speed, three-dimensional wind direction and vortex of a tested area.

* * * * *